(12) United States Patent
Mani et al.

(10) Patent No.: US 8,936,604 B2
(45) Date of Patent: Jan. 20, 2015

(54) PNEUMATIC SURGICAL INSTRUMENT AND CORRESPONDING METHODS FOR IMPLANTING, EXTRACTING AND REORIENTING ORTHOPEDIC IMPLANTS

(76) Inventors: Frederic Mani, Dully (CH); Thierry Monnier, Les Rousses (FR); Alain Lebet, Lausanne (CH)

(*) Notice: Subject to any disclaimer, the term of this patent is extended or adjusted under 35 U.S.C. 154(b) by 203 days.

(21) Appl. No.: 13/413,551

(22) Filed: Mar. 6, 2012

(65) Prior Publication Data

US 2012/0232562 A1 Sep. 13, 2012

Related U.S. Application Data

(60) Provisional application No. 61/449,934, filed on Mar. 7, 2011, provisional application No. 61/449,942, filed on Mar. 7, 2011, provisional application No. 61/449,948, filed on Mar. 7, 2011, provisional application No. 61/449,958, filed on Mar. 7, 2011, provisional application No. 61/596,193, filed on Feb. 7, 2012.

(51) Int. Cl.
| | |
|---|---|
| *A61B 17/58* | (2006.01) |
| *A61B 17/60* | (2006.01) |
| *A61F 2/00* | (2006.01) |
| *A61B 17/00* | (2006.01) |
| *A61B 17/16* | (2006.01) |
| *A61B 17/92* | (2006.01) |
| *A61F 2/46* | (2006.01) |

(Continued)

(52) U.S. Cl.
CPC ............. *A61B 17/1604* (2013.01); *A61B 17/92* (2013.01); *A61F 2/4609* (2013.01); *A61F 2/4612* (2013.01); *A61F 2/4637* (2013.01); *A61B 2017/00544* (2013.01); *A61B 2017/00548* (2013.01); *A61B 2017/922* (2013.01); *A61B 2017/924* (2013.01); *A61F 2/34* (2013.01); *A61F 2/3609* (2013.01); *A61F 2002/4619* (2013.01); *A61F 2002/4681* (2013.01); *A61F 2002/4694* (2013.01)
USPC ............................. 606/100; 606/99; 606/190

(58) Field of Classification Search
CPC ... A61F 2/4637; A61F 2/4609; A61F 2/4607; A61B 17/92
USPC .................. 606/171, 184, 185, 190, 99, 100; 433/118, 150; 173/221
See application file for complete search history.

(56) References Cited

U.S. PATENT DOCUMENTS

| | | |
|---|---|---|
| 2,275,102 A | 3/1942 | Fitzsimmons |
| 3,250,334 A | 5/1966 | Sussman |
| 4,016,873 A | 4/1977 | Anderson |

(Continued)

FOREIGN PATENT DOCUMENTS

| | | |
|---|---|---|
| EP | 0317507 | 4/1992 |
| EP | 1163882 | 9/2003 |

(Continued)

*Primary Examiner* — David Bates
(74) *Attorney, Agent, or Firm* — Woods Patent Law

(57) ABSTRACT

Various embodiments of components, devices, systems and methods are provided for a pneumatic surgical instrument having a probe or an impactor disposed at a distal end thereof and configured to make contact with a selected portion of an orthopedic implant or device. The instrument is configured to generate a shock wave, which is then transferred to the distal end of the probe or impactor, and then into the orthopedic implant or probe.

21 Claims, 14 Drawing Sheets

(51) Int. Cl.
*A61F 2/34* (2006.01)
*A61F 2/36* (2006.01)

(56) References Cited

U.S. PATENT DOCUMENTS

| | | | |
|---|---|---|---|
| 4,131,165 A | | 12/1978 | Walker et al. |
| 4,135,517 A | * | 1/1979 | Reale .................... 606/86 R |
| 4,150,656 A | * | 4/1979 | Curran ..................... 124/74 |
| 4,298,074 A | * | 11/1981 | Mattchen ................ 173/129 |
| 4,399,813 A | | 8/1983 | Bawber |
| 4,462,395 A | | 7/1984 | Johnson |
| 4,476,861 A | | 10/1984 | Dimakos |
| 4,716,890 A | | 1/1988 | Bichel |
| 5,057,112 A | | 10/1991 | Sherman |
| 5,108,400 A | | 4/1992 | Appel et al. |
| 5,160,336 A | | 11/1992 | Favre |
| 5,169,399 A | * | 12/1992 | Ryland et al. ............. 606/91 |
| 5,171,313 A | | 12/1992 | Salyor |
| 5,352,230 A | * | 10/1994 | Hood ........................ 606/99 |
| D362,503 S | | 9/1995 | Cook et al. |
| 5,449,363 A | | 9/1995 | Vrust et al. |
| 5,613,483 A | | 3/1997 | Lukas et al. |
| 5,626,584 A | | 5/1997 | Young |
| 5,906,623 A | | 5/1999 | Peterson |
| 5,980,528 A | | 11/1999 | Salys |
| 6,152,930 A | | 11/2000 | Mastrorio et al. |
| 6,585,771 B1 | * | 7/2003 | Buttermilch et al. ...... 623/22.12 |
| 7,048,073 B2 | | 5/2006 | Hezeltine |
| 7,326,217 B2 | | 2/2008 | Bubb |
| 7,407,070 B2 | | 8/2008 | Hazeltine |
| 7,470,274 B2 | | 12/2008 | Lebet |
| 7,485,149 B1 | | 2/2009 | White |
| 7,569,057 B2 | | 8/2009 | Liu et al. |
| 7,604,637 B2 | | 10/2009 | Johnson et al. |
| 7,811,256 B2 | | 10/2010 | Landman et al. |
| 2002/0010486 A1 | | 1/2002 | Hirt |
| 2003/0000774 A1 | | 1/2003 | Highley |
| 2003/0065398 A1 | * | 4/2003 | Cueille et al. ............... 623/22.4 |
| 2003/0229357 A1 | * | 12/2003 | Dye ............................ 606/99 |
| 2006/0069395 A1 | | 3/2006 | Lebet |
| 2006/0100553 A1 | | 5/2006 | Lodin |
| 2009/0118741 A1 | | 5/2009 | Lebet |
| 2010/0305624 A1 | * | 12/2010 | Lozier et al. ............. 606/86 R |
| 2012/0022545 A1 | | 1/2012 | Lebet |

FOREIGN PATENT DOCUMENTS

| | | |
|---|---|---|
| WO | WO 95/22934 | 8/1995 |
| WO | WO 98/26705 | 6/1998 |

* cited by examiner

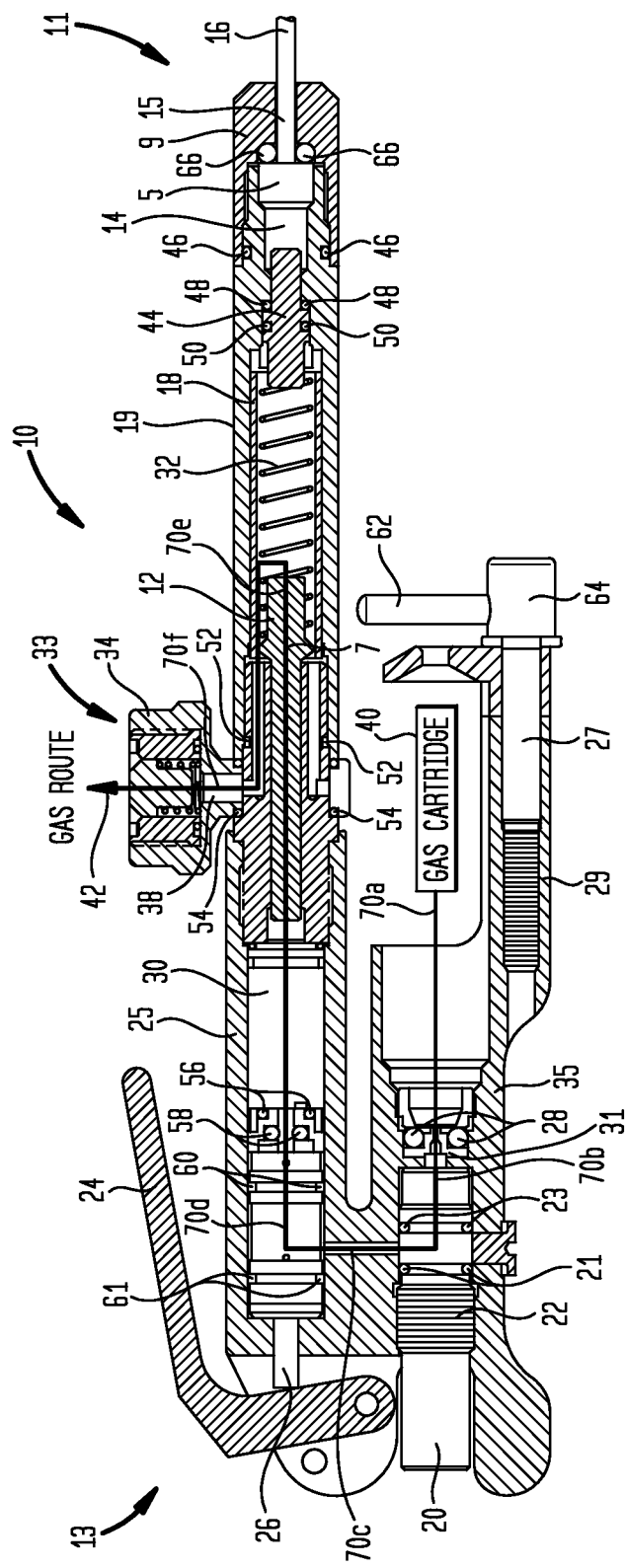
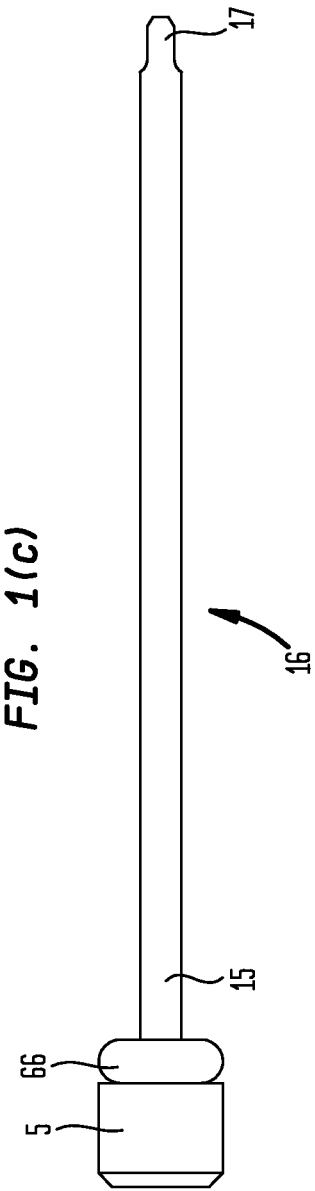

RISE-TIME AND FORCE OF THE ORTHOSHOCK™ vs THE HAMMER

RISE-TIME AND FORCE OF THE ORTHOSHOCK™ vs THE HAMMER

AVERAGE PEAK FORCE WITH ERROR BARS

AVERAGE RISE-TIME WITH ERROR BARS

PNEUMATIC SURGICAL INSTRUMENT AND CORRESPONDING METHODS FOR IMPLANTING, EXTRACTING AND REORIENTING ORTHOPEDIC IMPLANTS

RELATED APPLICATIONS

This application claims priority and other benefits from each of: (1) U.S. Provisional Patent Application Ser. No. 61/449,934 entitled "Pneumatic Instrument for Artificial Bone Markers and Therapy" to Mani et al. filed Mar. 7, 2011; (2) U.S. Provisional Patent Application Ser. No. 61/449,942 entitled "Pneumatic Instrument Bone Resection, Anchor Fixation, Arthroscopy, Osteotomy, Generating Microfractures" to Mani et al. filed Mar. 7, 2011; (3) U.S. Provisional Patent Application Ser. No. 61/449,948 entitled "Pneumatic Instrument of Hip and Ball Joint and Bone Cement" to Mani et al. filed Mar. 7, 2011; (4) U.S. Provisional Patent Application Ser. No. 61/449,958 entitled "Pneumatic Instrument for Bone Revision and Implant Removal" to Mani et al. filed Mar. 7, 2011, and (5) U.S. Provisional Patent Application Ser. No. 61/596,193 entitled "Pneumatic Surgical Instrument Configured to Deliver Shock Wave Having Fast Rise Time and Increased Energy" to Mani et al. filed Feb. 7, 2012. Each of the foregoing provisional patent applications is hereby incorporated herein, each in its respective entirety. U.S. patent application Ser. No. 13/413,455 entitled "Pneumatic Surgical Instrument and Corresponding Methods for Penetrating, Resecting and Microfracturing Bone" to Mani et al. filed on even date herewith is also hereby incorporated by reference herein in its entirety.

FIELD OF THE INVENTION

Various embodiments of the invention described herein relate to the field of surgical instrumentation, and more particularly to components, devices, systems and methods associated with a pneumatic surgical instrument configured to deliver accurate focused impact forces to selected portions of orthopedic implant devices such as artificial hip and shoulder joints, and devices and components associated therewith.

BACKGROUND

Various problems can occur when surgically implanting, removing, modifying and/or adjusting orthopedic implants in human beings. When engaging in such surgical procedures, it is necessary that physicians sometimes employ hammers to provide impulse forces to selected portions of orthopedic implants. For example, during the installation, extraction, or reorientation or adjustment of portions of an artificial hip or shoulder joint, a hammer may be employed to lock a portion of the joint in place, to move, adjust the position of or reorient a portion of the joint, or to remove or extract a portion of the joint. It is well known that artificial orthopedic hip and shoulder joints or implants can be difficult to install, extract or reorient. The delivery of impulse forces by means of a hammer to orthopedic implants is also known to have several problems, including: (a) a variable amount of force being delivered with each hammer blow; (b) an inability to finely gauge or control the amount of force that is delivered by a hammer; (c) different physicians applying different amounts of force with a hammer; (d) locational inaccuracy with respect to where hammer blows actually fall, and (e) other factors not specifically enumerated here but that are known to those skilled in the art.

What is needed is a surgical instrument that eases the installation, extraction and reorientation of artificial hip, shoulder or other types of artificial joints or joint components.

SUMMARY

In one embodiment, there is provided a pneumatic surgical instrument, comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, wherein the probe has a distal end configured and shaped to engage: (a) at least a portion of a surface of an orthopedic implant, (b) a device configured to be placed between the orthopedic implant and the distal end of the probe, or (c) an orthopedic implant impactor configured to receive the distal end of the probe therein or thereon, the impactor being configured and shaped to engage at least a portion of the surface of the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe being substantially repeatable by the instrument when the trigger is actuated again by the user.

In another embodiment, there is provided an orthopedic implant configured for use with a pneumatic surgical instrument comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage: (a) at least a portion of the surface of the orthopedic implant, or (b) an orthopedic implant impactor configured to receive the distal end of the probe therein or thereon, the impactor being configured and shaped to engage at least a portion of the surface of the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe being substantially repeatable by the instrument when the trigger is actuated again by the user, the surface of the orthopedic implant comprising at least one recess or protrusion disposed thereon and configured to mateably engage the distal end of the probe or a portion of the impactor.

In yet another embodiment, there is provided an orthopedic implant system comprising an orthopedic implant having a surface, a pneumatic surgical instrument comprising a striker disposed within a longitudinal striker sleeve, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage: (a) at least a portion of the surface of the orthopedic implant, or (b) an orthopedic implant impactor configured to receive the distal end of the probe therein or thereon, the impactor being configured and shaped to engage at least a portion of the surface of the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe being substantially repeatable by the instrument when the trigger is actuated again by the user, wherein the surface of the orthopedic implant comprises at least one recess or protrusion disposed thereon that is configured to mateably engage the distal end of the probe or a portion of the impactor.

In still another embodiment, there is provided a method of generating and delivering a shockwave to an orthopedic implant with a pneumatic surgical instrument having a distal end, the surgical instrument comprising a striker disposed within a longitudinal striker sleeve of the instrument, a removable probe mountable on a distal end of the instrument, a pressure regulator operably connectable to a gas cartridge mountable on or in the instrument, a trigger mechanism comprising a trigger, the trigger mechanism being operably connected to the pressure regulator and to the striker, the probe having a distal end configured and shaped to engage: (a) at least a portion of a surface of an orthopedic implant, or (b) an orthopedic implant impactor configured and shaped to engage at least a portion of the surface of the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe being substantially repeatable by the instrument when the trigger is actuated again by the user, the method comprising positioning the distal end of the probe or the impactor in contact with at least a portion of the surface orthopedic implant, and actuating the trigger mechanism to deliver the shockwave to the probe and thence to the orthopedic implant.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

FIG. 1(b) shows a cross-sectional view according to one embodiment of pneumatic surgical instrument 10;

FIG. 1(c) shows a side view according to one embodiment of probe 16;

The drawings are not necessarily to scale. Like numbers refer to like parts or steps throughout the drawings.

DETAILED DESCRIPTIONS OF SOME EMBODIMENTS

Figure 1A:
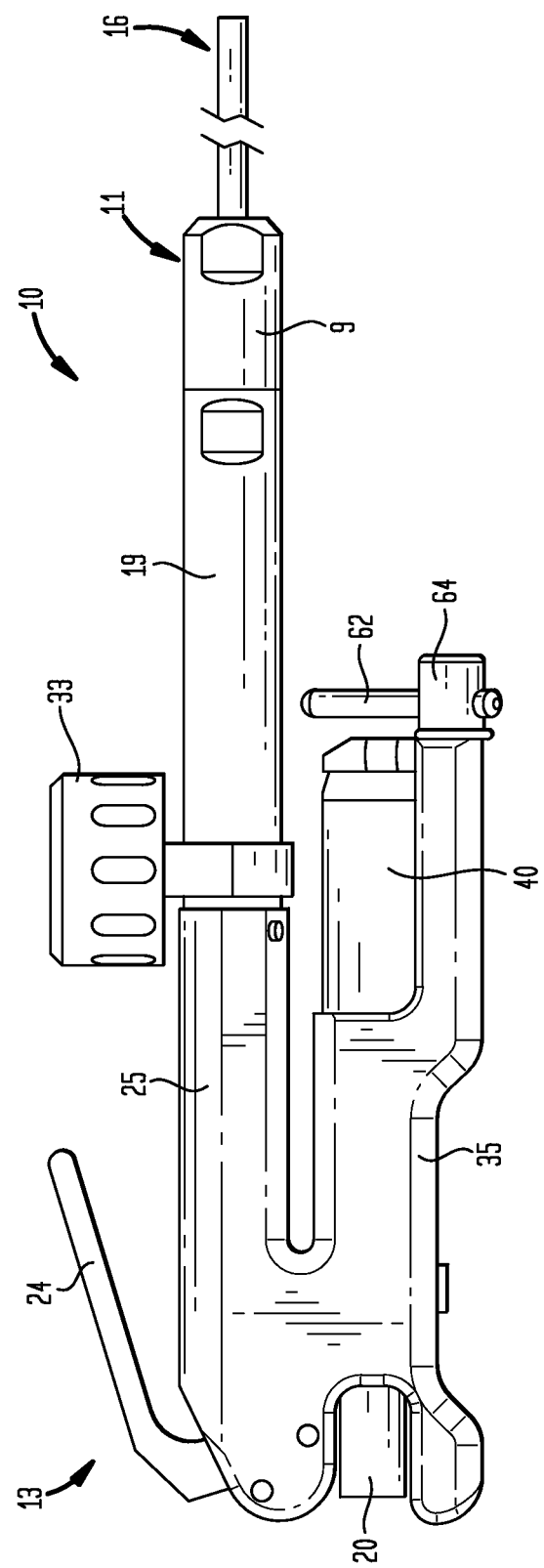
FIG. 1(a) shows a side view according to one embodiment of pneumatic surgical instrument 10.
Figure 1D:
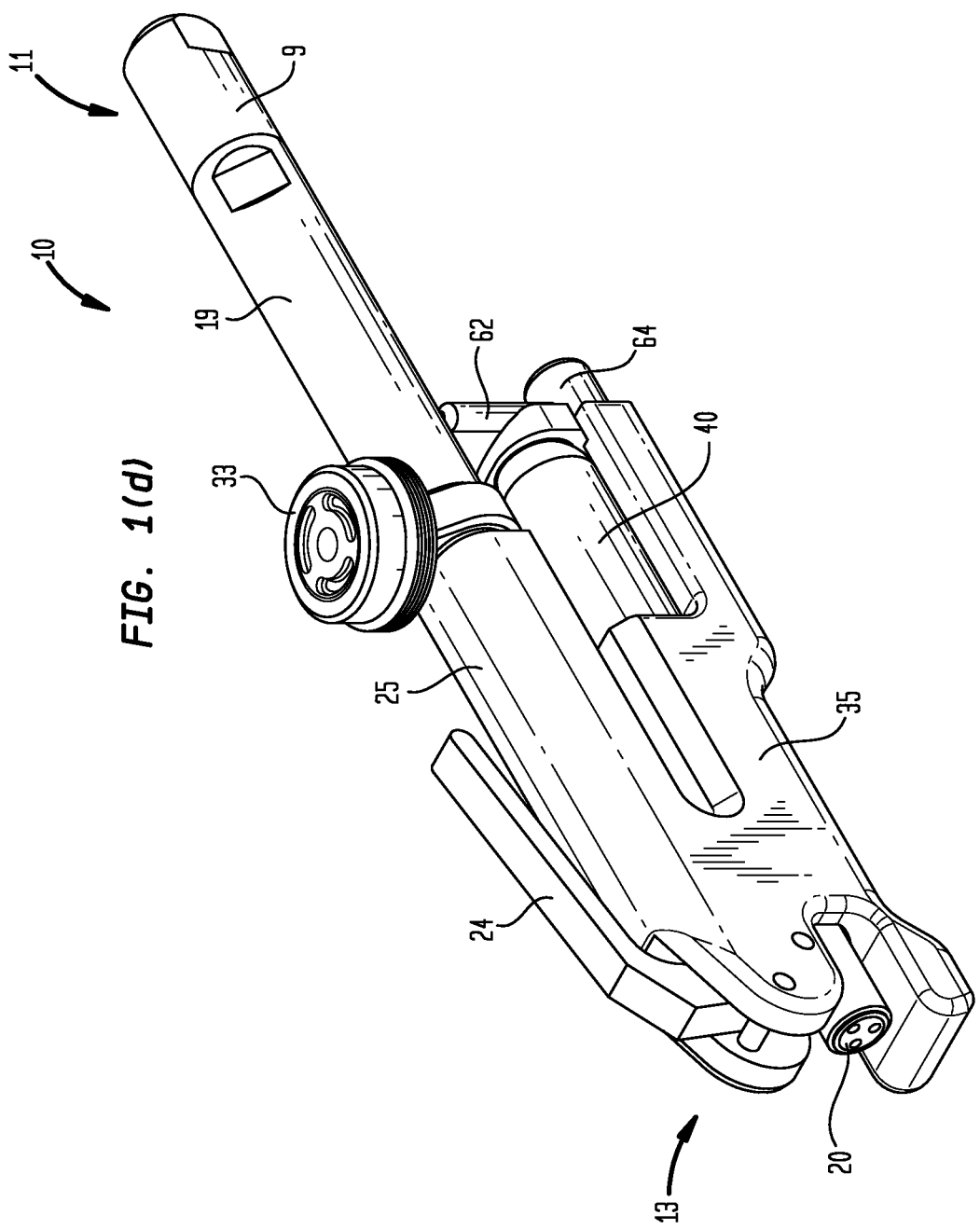
FIG. 1(d) shows a top rear perspective view according to one embodiment of pneumatic surgical instrument 10.

Referring now to FIGS. 1(a), 1(b) and 1(d), there are shown side, cross-sectional and top rear perspective views according to one embodiment of pneumatic surgical instrument 10, a commercial embodiment of which is known by the name OrthoShock™ and manufactured by OrthoWin™ of Gland, Switzerland. As shown in FIGS. 1(a), 1(b), 1(c) and 1(d), pneumatic surgical instrument 10 comprises striker 12, which in one embodiment is a piston. Removable probe or shockwave transfer device 16 is mountable on distal end 11 of instrument 10. Pressure regulator 20 is operably connectable to gas cartridge 40, which is mountable on or in instrument 10. According to one embodiment, gas cartridge 40 is a medical-grade $CO_2$ cartridge. Further according to one embodiment, trigger mechanism 30 comprises trigger or trigger handle 24, and trigger mechanism 30 is operably connected to pressure regulator 20 and striker 12. According to one embodiment, instrument 10 includes front metal housing 19, rear top metal housing 25, and rear bottom housing 35.

FIG. 1(c) shows a side view according to one embodiment of probe 16, where O-ring 66 is pre-mounted on proximal end 15 of the shaft projecting towards distal end 17 from a distal surface of proximal probe terminus 5. According to various embodiments, and as discussed in further detail below, the thickness, mechanical properties or materials, stiffness, or other properties of O-ring 66 may be selected to provide a desired amount of displacement or other desired performance characteristics when surgical instrument 10 is triggered or actuated. In addition, instrument 10 may be configured to receive more than one O-ring 66 between proximal terminus 5 and probe cap 9.

Figure 2A:
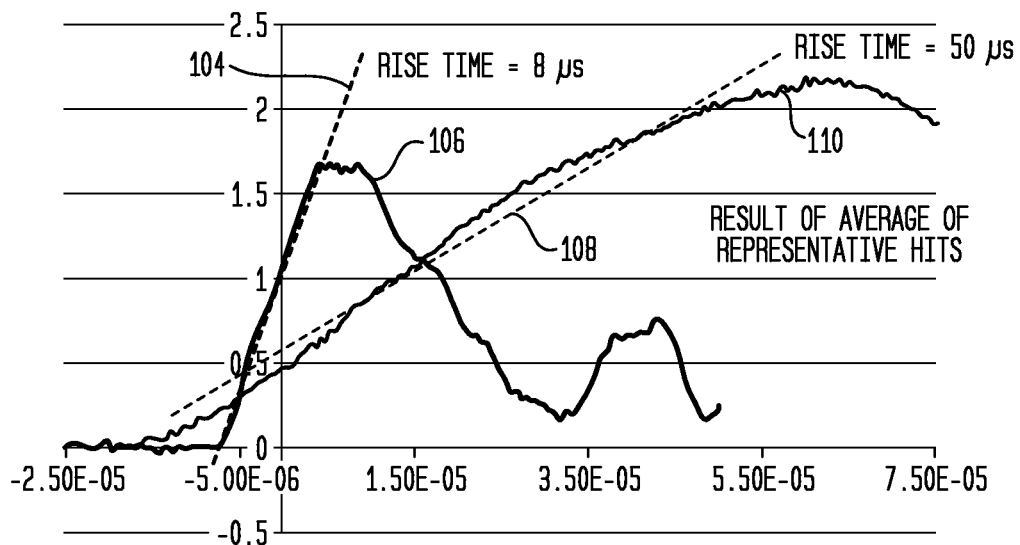
FIGS. 2(a) through 2(e) show various characteristics of the rise times and forces of the shock waves generated by a commercial embodiment of instrument 10 of FIGS. 1(a) through 1(c)
Figure 2B:
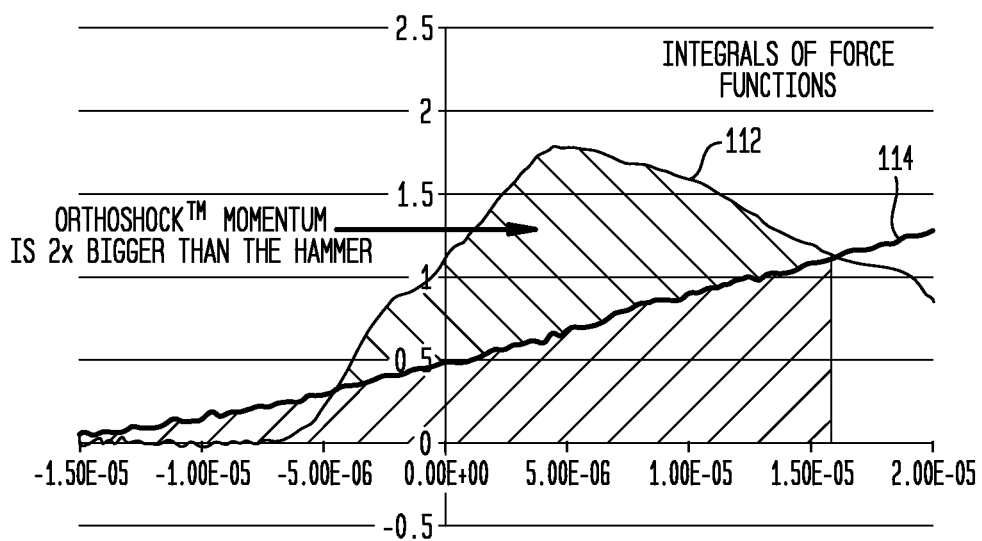
Figure 2C:
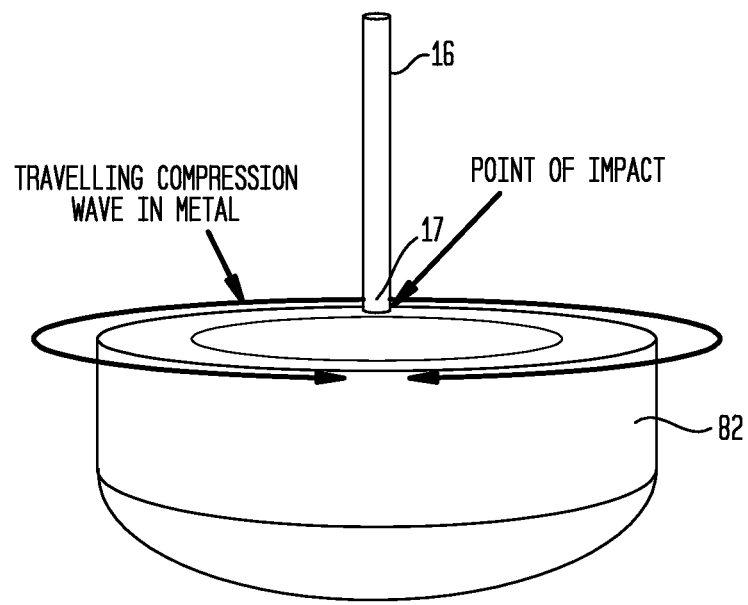
Figure 2D:
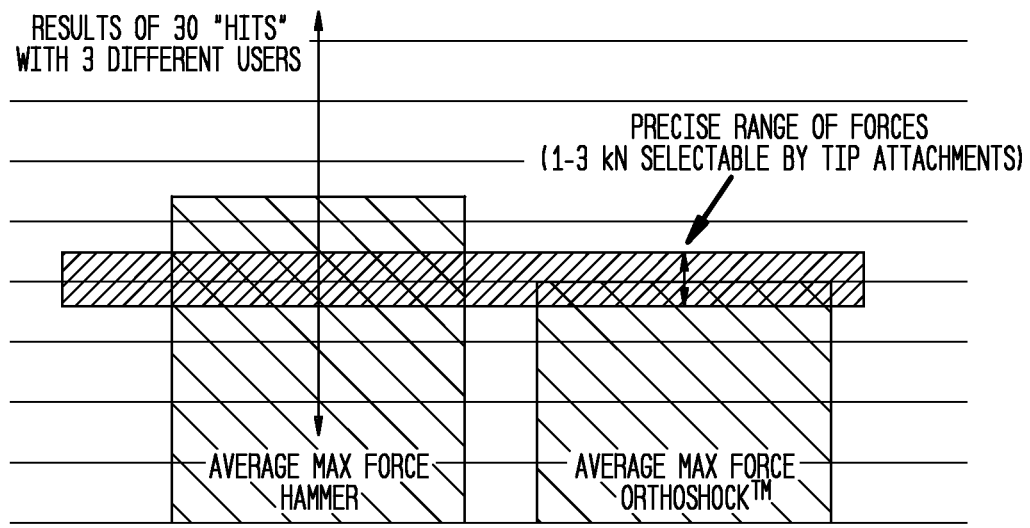
Figure 2E:
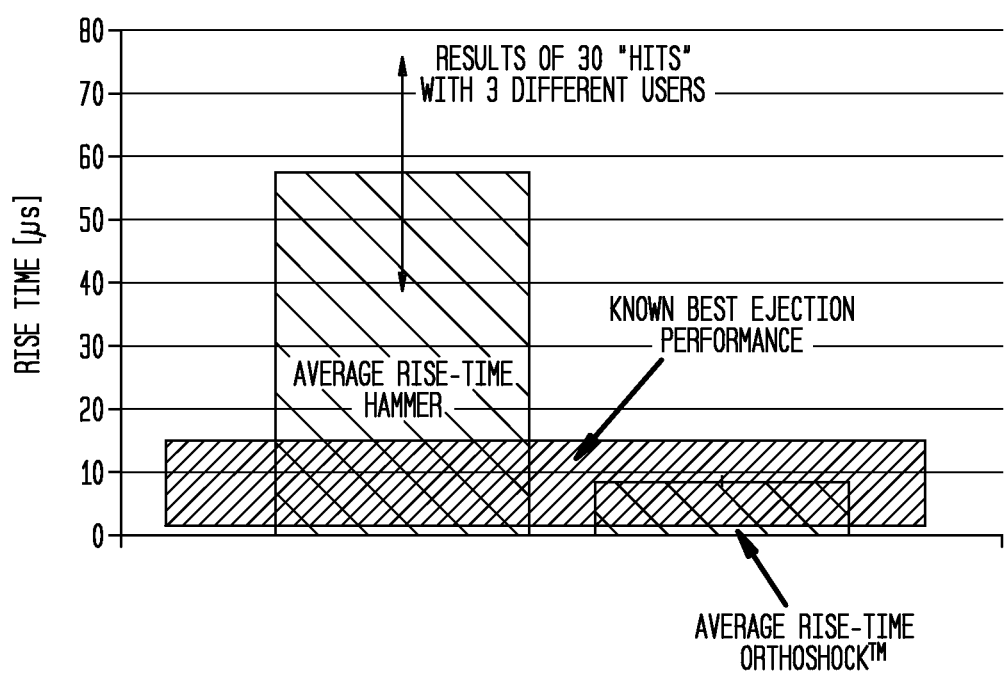
Figure 3A:
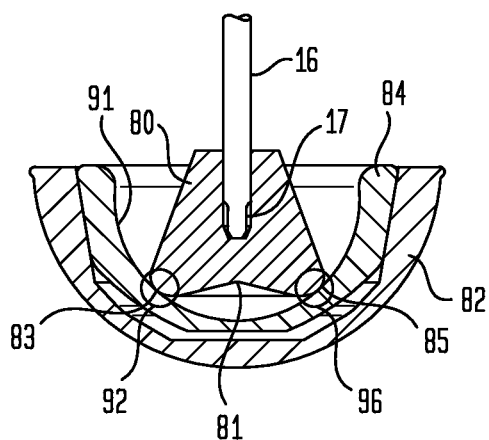
FIGS. 3(a) through 3(e) show various cross-sectional views of an artificial orthopedic hip implant cup or socket 82 and corresponding orthopedic hip insert 84 in conjunction with one embodiment of distal end 17 of probe 16 inserted in a proximal end of one embodiment of orthopedic implant impactor 80.
Figure 3B:
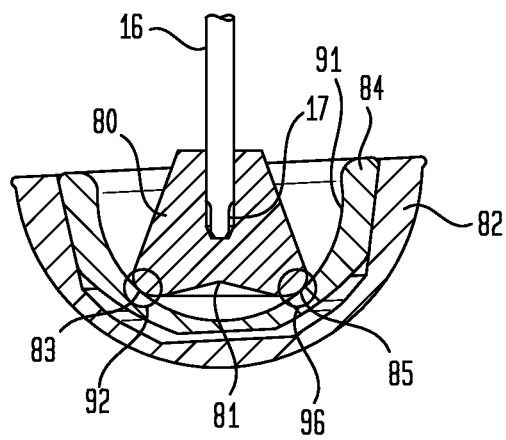
Figure 3C:
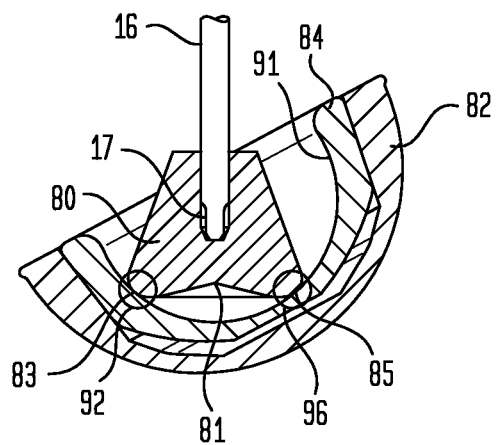
Figure 3D:
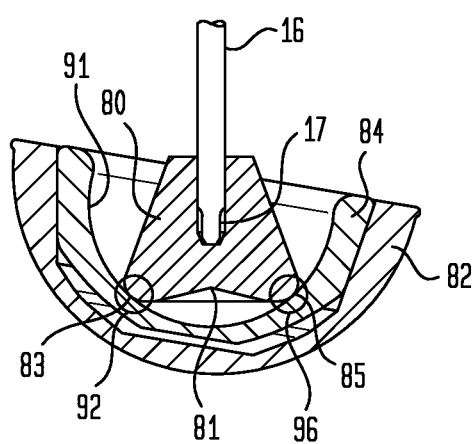
Figure 3E:
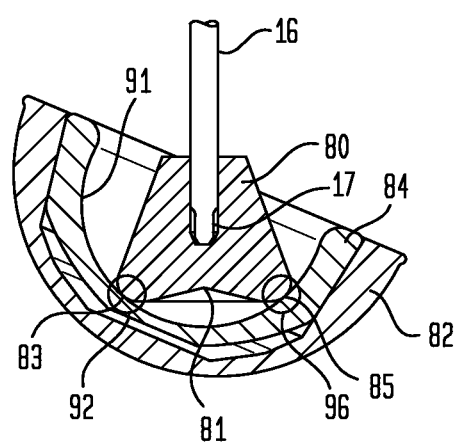

Continuing to refer to FIGS. 1(a) through 1(d), probe 12 has distal end 17 configured and shaped to engage: (a) at least a portion of a surface of an orthopedic implant 82, 84, 88, 90, 122, 124, or 126 (see, for example, FIG. 2(c) herein), (b) a device such as a punch configured to be placed between the orthopedic implant and the distal end of the probe (not shown in the Figures), or (c) an orthopedic implant impactor 80 configured to receive distal end 17 of probe 16 therein or thereon (see, for example, FIGS. 3(a) through 5(b) herein).

According to some embodiments, impactor 80 is configured and shaped to engage at least a portion of the surface of an orthopedic implant. Instrument 10 is configured to deliver at least one shock wave to probe 16 when trigger 24 is actuated by a user and a predetermined volume of gas stored at a predetermined range of pressures in instrument 10 is released thereby to cause striker 12 to move towards distal end 11 of instrument 10 and deliver the shock wave to proximal end 15 of probe 16.

The shockwave delivered by instrument 10 and probe 16 is substantially repeatable by instrument 10 when trigger 24 is actuated again by the user for the delivery of a subsequent shockwave by instrument 10 after the volume of gas exhausted by instrument 10 through gas exhaust device 33 has been replenished within instrument 10 from gas cartridge 40 through gas regulator 20.

According to one embodiment, the predetermined volume of gas stored at a predetermined range of pressures is contained in a chamber disposed within trigger mechanism 30, and is released to force the striker towards distal end 11 of instrument 10 when trigger mechanism 30 is actuated by the user by means of trigger handle 24 and actuator 26. Other means of triggering trigger mechanism 30 are contemplated, such as solenoids, mechanically depressible buttons, and so on. Moreover, the chamber containing the predetermined volume of gas stored at a predetermined range of pressures in instrument 10 may be housed elsewhere in instrument 10 other than as part of trigger mechanism 30, such as, by way of example, in a chamber disposed in or attached to pressure regulator 20, or in another location within or on instrument 10. Note that in the embodiment of instrument 10 shown in FIGS. 1(a), 1(b) and 1(c), striker 12 is disposed within longitudinal striker sleeve 18, although other embodiments are contemplated.

Further according to various embodiments, pneumatic instrument 10 may be configured such that the shockwave provided by probe 16 has a rise time ranging between about 2 microseconds and about 20 microseconds, between about 4 microseconds and about 16 microseconds, or between about 6 microseconds and about 10 microseconds, and that instrument 10 may further be configured to cause the shock wave delivered by probe 16 to an orthopedic implant to travel from a first side of the orthopedic implant to a second opposing side of the orthopedic implant is less than about 30 microseconds, or less than about 20 microseconds, more about which is said below. Other rise times are also contemplated.

Referring still to FIGS. 1(a) through 1(d), and according to one embodiment, instrument 10 comprises removable probe cap 9, which is configured to receive proximal end 15 of probe 16 therein or therethrough, where probe cap 9 is mountable on distal end 11 of instrument 10, and where proximal probe terminus 5 is located proximally within instrument 10 behind probe cap 9. Firing pin 44 is disposed between a distal end of striker 12 and a proximal end of firing pin receiver 14. The distal end of striker 12 is configured to engage and strike a proximal end of firing pin 44 and drive same towards firing pin receiver 14, which is configured to receive the distal end of firing pin 44 therein and transfer the shockwave delivered thereby to proximal probe terminus 5.

As further shown in FIG. 1(c), probe O-ring 66 is disposed near proximal end 15 of probe 16 between an inner surface of probe cap 9 and a distal portion of probe terminus 5. In one embodiment, probe O-ring 66 comprises nitrile and has a thickness ranging between about 2 mm and about 3 mm, although other ranges of the thickness of O-ring 66 are contemplated, such as between about 1 mm and about 6 mm, between about 1.5 mm and about 5 mm, between about 2 mm and about 4 mm. In one embodiment, O-ring 66 has an inner diameter of about 2.8 mm, an outer diameter of about 7 mm, and a thickness of 2.64 mm. According to one embodiment, probe 16 is displaced by about 0.5 mm when instrument 10 is actuated. Other amounts of the displacement of probe 16 when instrument 10 is triggered or actuated may be provided, however, such as displacement of about 0.2 mm, about 0.4 mm, about 0.6 mm, about 0.8 mm, and about 1 mm.

In conjunction with the amount of force provided by the distal end of striker 12 to firing pin 44, firing pin receiver 14, and probe terminus 5, the number, thickness or other properties of O-rings 66 may be configured to provide a desired amount of displacement of probe 16, or a desired force or energy signature, when instrument 10 is triggered. Further according to some embodiments, other O-rings 46, 48, 50, 52, 54, 56, 58, 60, 61, 21, 23 and 28 in instrument 10 may also comprise nitrile, which does not absorb $CO_2$ gas and thus prevents the degradation or expansion of such O-rings caused by exposure to $CO_2$ gas.

Still referring to FIG. 1(b), and according to one embodiment, pressure regulator 20 includes a pin 31 that is configured to puncture gas cartridge 40 when replaceable gas cartridge 40 is mounted in or on instrument 10. Gas cartridge 40 may be inserted or removed form instrument 10 by turning gas cartridge replacement and removal mechanism handle 62, and corresponding shaft end 64, rod 27, and threaded portion 29 inwardly or outwardly, as the case may be. Pressure regulator 20 directs and regulates the pressure of gas originating in cartridge 40 to trigger mechanism 30, and includes spring 22, which is configured to push a valve located in pressure regulator 20 closed after a predetermined amount or volume of gas has been emitted from cartridge 40 into pressure regulator 20 and trigger mechanism 30. According to some embodiments, gas regulator 20 is configured to provide pressurized gas to trigger mechanism 30 at pressures ranging between about 15 bars and about 60 bars, or between about 25 bars and about 35 bars. A nominal regulated pressure of 29 bars is preferred according to one embodiment.

Continuing to refer to FIG. 1(b), there are shown interconnected gas passageways 70a, 70b, 70c, 70d, 70e, and 70f, which are routed, respectively, through gas cartridge 40, gas regulator 20, between gas regulator 20 and trigger mechanism 30, trigger mechanism 30, striker 12 (through central aperture 7), and around the top portion of striker 12. Gas travelling through such passageways is ultimately exhausted through gas exhaust device 33 as exhaust gas 42. According to one embodiment, and as shown in FIG. 1(b), gas exhaust device 33 comprises gas exhaust filter housing 34, a replaceable gas exhaust filter cartridge (not shown in the drawings), and gas exhaust filter valve 38. Gas exhaust device 33 is configured to trap particulate contaminants in the replaceable gas exhaust filter cartridge that may be present in gas provided by gas cartridge 40, and prevent contamination of the sterile field during a surgical procedure.

Referring to FIGS. 1(a) through 1(d), and according to one embodiment, probe 16 comprises a metal or metal alloy such as stainless steel, and has a length ranging between about 10 cm and about 30 cm, and a diameter ranging between about 2.8 mm and about 3.4 mm. Other probe lengths and diameters are also contemplated. Distal end 17 of probe 16 may be configured to accept an orthopedic implant impactor 80 (see subsequent Figures) thereon or therein, and/or may be configured to engage a portion of a surface of an orthopedic implant directly.

Referring now to FIGS. 2(a) through 2(e), there are shown various characteristics of the rise times and forces of the shock waves generated by a commercial embodiment of instrument 10 of FIGS. 1(*a*) through 1(*d*) known as the OrthoShock™ surgical instrument. As illustrated in FIG. 2(*a*), there is shown the output signal (or shockwave or impulse force) delivered according to one embodiment of the OrthoShock surgical instrument disclosed and described herein. The shockwave or impulse force output signal delivered by an OrthoShock™ surgical instrument to an orthopedic implant or device is juxtaposed with the output signals provided by a conventional orthopedic hammer. As will be seen by referring to FIG. 2(*a*), the rise time, or the amount of time over which the shockwave or impulse force is provided by instrument 10 is much shorter than that provided by a conventional orthopedic hammer. In the example shown in FIG. 2(*a*), the total rise time is about 6 microseconds, as compared to a 50 microsecond rise time characteristic of a hammer employed for the same purpose. The steeper the curve of the output signal, the better the initial impulse. Further as shown in FIG. 2(*a*), the rise time of the OrthoShock™ surgical instrument is about five times greater than that of a corresponding orthopedic hammer.

FIG. 2(*b*) shows a comparison of integrated output shockwave or impulse force output signals provided by one embodiment of the surgical instrument described and disclosed herein relative to those provided by a hammer, and corresponds to the results shown in FIG. 2(*a*). The greater the integral, especially during the first 20 microseconds in the context of delivering shockwave to an artificial hip implant insert for the purpose of ejecting same, the bigger the change in momentum, and the more energy that is usefully transferred to the orthopedic implant or device to cause its ejection from an artificial hip socket. This means that use of surgical instrument 10 disclosed and described herein results in particularly efficacious and easy removal, reorientation or insertion of an artificial hip implant insert with respect to an artificial hip implant socket.

FIG. 2(*c*) shows one embodiment of a travelling shock- or compression wave in an orthopedic implant 82 provided by the surgical instrument described and disclosed herein. Surgical instrument 10 described and disclosed herein has been discovered to cause a shockwave to travel from one side of an orthopedic implant insert to the opposite side in about 20 microseconds.

FIGS. 2(*d*) and 2(*e*) show rise time results obtained with one embodiment of surgical instrument 10 described and disclosed herein in comparison to those obtained with a hammer. As shown in FIGS. 2(*d*) and 2(*e*), surgical instrument 10 described and disclosed herein provides much smaller rise times and improved orthopedic implant insert ejection performance relative to a conventional hammer. Repeatability and ejection performance are markedly improved.

Referring now to FIGS. 3(*a*) through 3(*e*), there are shown various cross-sectional views of an artificial orthopedic hip implant cup or socket 82 and corresponding orthopedic hip insert 84 in conjunction with one embodiment of distal end 17 of probe 16 inserted in a proximal end of one embodiment of orthopedic implant impactor 80, which is shown inserted and in contact with insert 84. Orthopedic implant impactor 80 shown in FIGS. 3(*a*) through 3(*e*) comprises first distal convex surfaces 83 and 85 having first compound radii 92 and 96 configured to engage corresponding concave surfaces of insert 82. The shapes of first distal convex surfaces 83 and 85 and first compound radii 92 and 96 are such that surfaces 83 and 85 result in impactor 80 being a "universal impactor" that can be used in conjunction with orthopedic hip implant sockets or cups, or orthopedic hip implant liners employed in artificial hip implant assemblies, that are of varying shapes and radii, and/or that are provided by different manufacturers of such implants that have different shapes and configurations.

According to one embodiment, such first distal convex surfaces 83 and 85 and first compound radii 92 and 96 are configured to engage the corresponding concave surfaces of the orthopedic implant 82 along a substantially continuous line of contact, thereby permitting better and more efficient mechanical coupling of impactor 80 to implant 84 for the delivery of shockwaves thereto during implantation, extraction or reorientation of implant 84 with instrument 10.

Figure 4A:
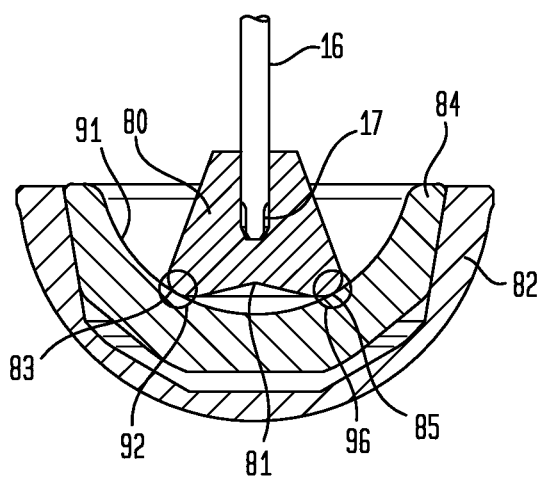
FIGS. 4(a) through 4(c) show one embodiment of impactor 80 and convex surfaces 83 and 85 of an orthopedic implant 84.
Figure 4B:
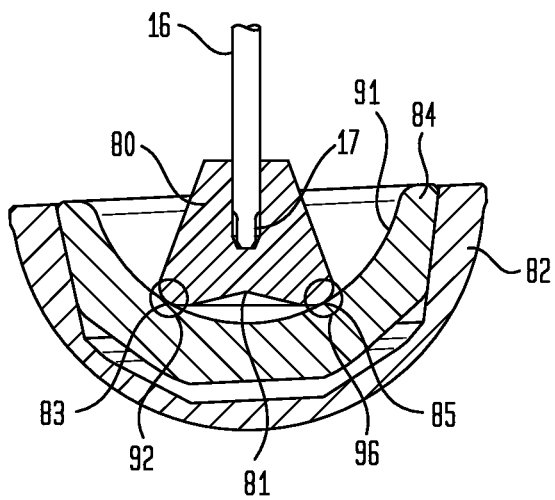
Figure 4C:
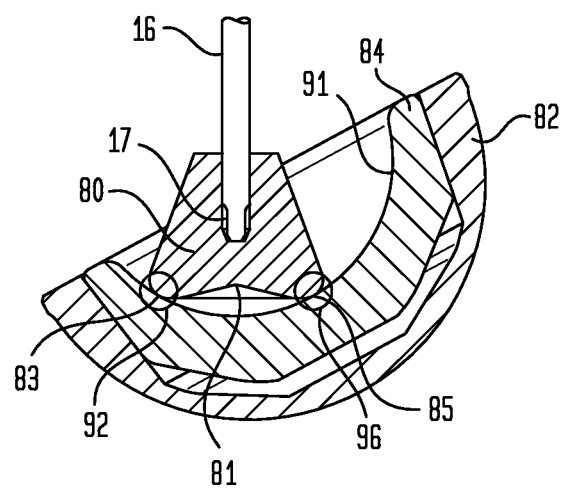

The "universal" adaptability of impactor 80 to implants 84 having different curvatures is shown by referring to FIGS. 4(*a*) through 4(*c*), where impactor 80 and convex surfaces 83 and 85 engage implant 84 and permit the implantation, extraction or reorientation of same despite the change in curvature of implant 84 with respect to implant 84 shown in FIGS. 3(*a*) through 3(*e*). As shown in FIGS. 3(*a*) through 4(*c*), a substantially continuous line of contact is maintained with implant 84 by the distal end of impactor 80 despite changes in the orientation of insert 84 with respect to underlying socket or cup 82, and despite changes in the curvature and shape of insert 84. Note, however, that in use it is preferred that impactor 80 and probe 16 be aligned at right angles to the surface of the orthopedic implant that is to be implanted, extracted or reoriented.

Impactor 88 may be used in similar fashion to implant, extract or reorient an orthopedic implant hip liner disposed atop an orthopedic hip implant insert 84 disposed between the liner and the underlying cup or socket 84. Such inserts are often formed of ceramic, as is well known in the art. See, for example, orthopedic ceramic inserts provided by Ceramtec™ of Klopingen, Germany.

Figure 5A:
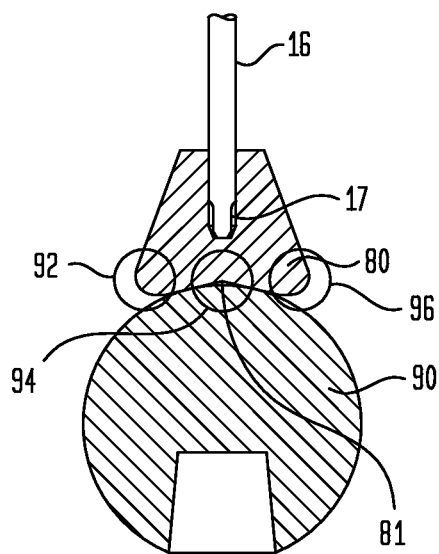
FIGS. 5(a) and 5(b) show one embodiment of orthopedic implant impactor 80 comprising second distal concave surfaces 81 having second compound radii 94 configured to engage corresponding convex surfaces of orthopedic implant 90.
Figure 5B:
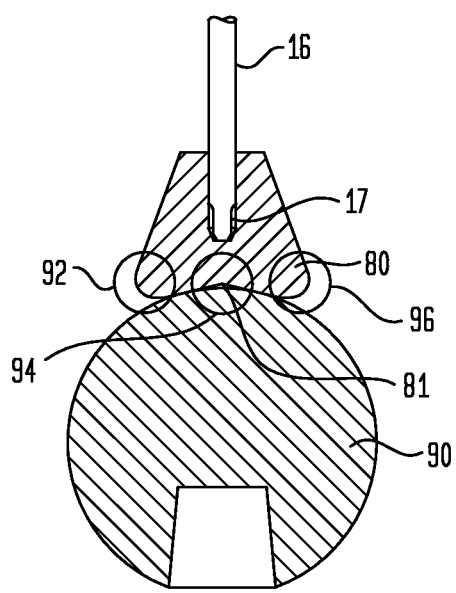

Referring now to FIGS. 5(*a*) and 5(*b*), orthopedic implant impactor 80 may further comprise second distal concave surfaces 81 having second compound radii 94 configured to engage corresponding convex surfaces of an orthopedic implant 90, which in the case of FIGS. 5(*a*) and 5(*b*) is an orthopedic ball 90 configured to mate with a corresponding orthopedic implant insert 82 or liner. Such second distal convex surfaces 81 and second compound radii 94 are configured to engage the corresponding concave surfaces of orthopedic implant 90 along a substantially continuous line of contact, thereby permitting better and more efficient mechanical coupling of impactor 80 to implant 90 for the delivery of shockwaves thereto during implantation, extraction or reorientation of implant 90 with instrument 10.

Figure 6A:
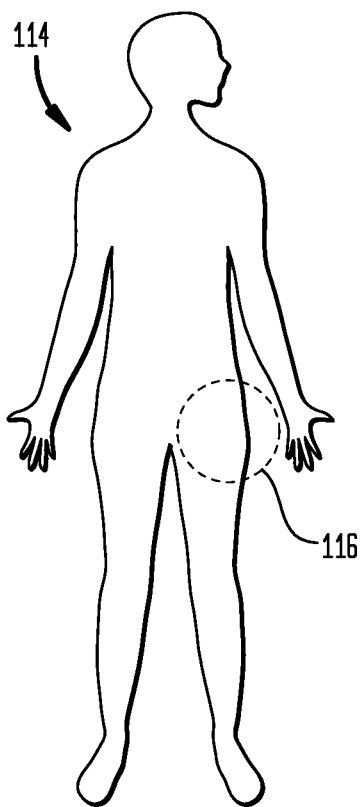
FIG. 6(a) shows a representative view of patient 114 having an artificial hip assembly implanted therein at hip site 116.
Figure 6B:
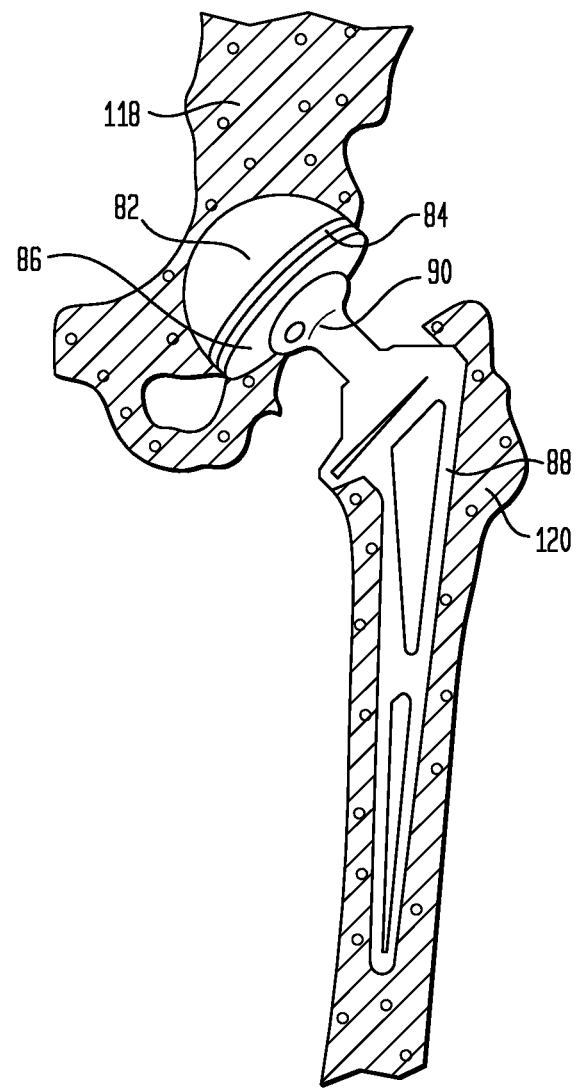
FIG. 6(b) shows an artificial hip assembly comprising stem 88 implanted in femur 120, cup or socket 82 implanted in pelvis 118, liner 86 implanted conformably within insert 84, and insert 84 implanted conformably in insert 84.
Figure 7A:
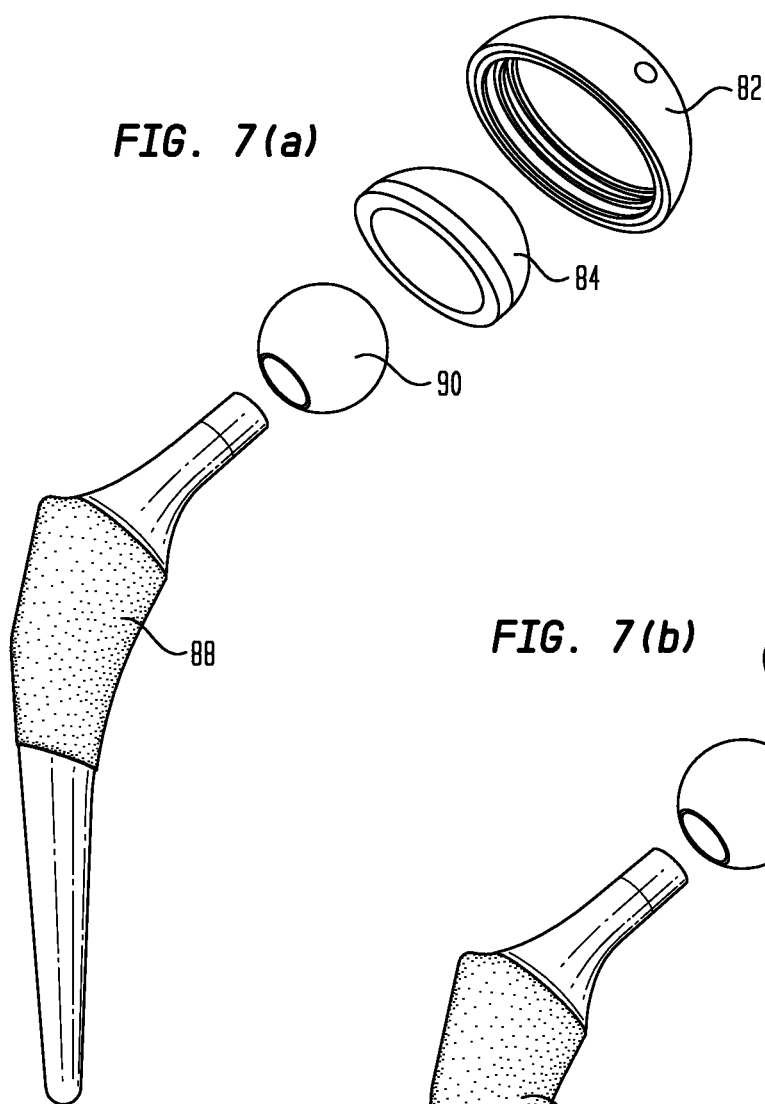
FIGS. 7(a) and 7(b) show two different embodiments of components of an artificial hip assembly.
Figure 7B:
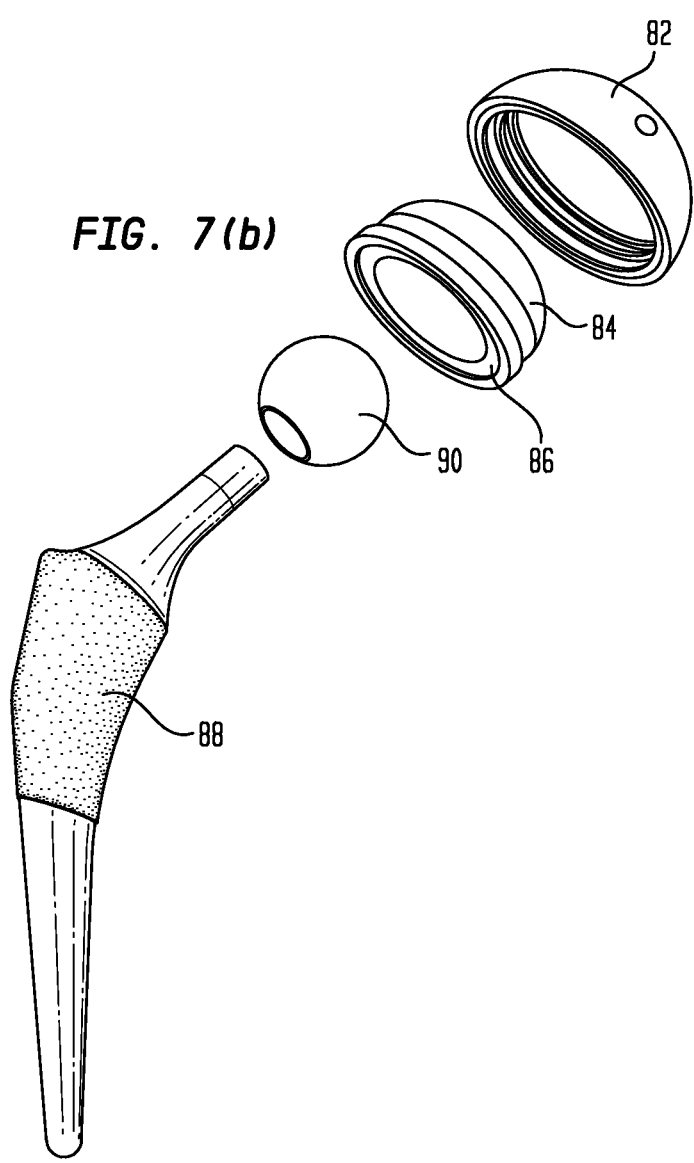

Referring now to FIGS. 6(*a*), there is shown a representative view of patient 114 having an artificial hip assembly implanted therein at hip site 116. As shown in FIG. 6(*b*), the artificial hip assembly comprises stem 88 implanted in femur 120, cup or socket 82 implanted in pelvis 118, liner 86 implanted conformably within insert 84, and insert 84 implanted conformably in insert 84. The components of an artificial hip assembly according to one embodiment, namely stem 88, ball 90, insert 84, and cup or socket 82, are shown in FIG. 7(*a*). The components of an artificial hip assembly according to another embodiment, namely stem 88, ball 90, liner 86, insert 84, and cup or socket 82 are shown in FIG. 7(*b*). All of orthopedic implants or components stem 88, ball 90, liner 86, insert 84, and/or cup or socket 82 shown in FIGS. 7(*a*) and 7(*b*) may be implanted, extracted or reoriented or adjusted using surgical instrument 10 described and disclosed herein, with or without impactor 80. In another embodiment, surgical instrument 10, probe 16, optionally impactor 80, and the orthopedic implant that is to be implanted, extracted or reoriented, may be configured and shaped such that a predetermined number of sequentially-delivered shock waves are required to implant, extract or reorient the implant.

By way of example, only one or two strikes delivered by instrument 10 to a liner 86 or insert 84 may be required to extract liner 86 and/or insert 84 from cup or socket 82. Several strikes may be required to implant or place securely a liner 86 and/or insert 84 in cup or socket 82. Multiple strikes may be required to reorient a liner 86 and/or insert 84, or cup or socket 82.

Figure 8A:
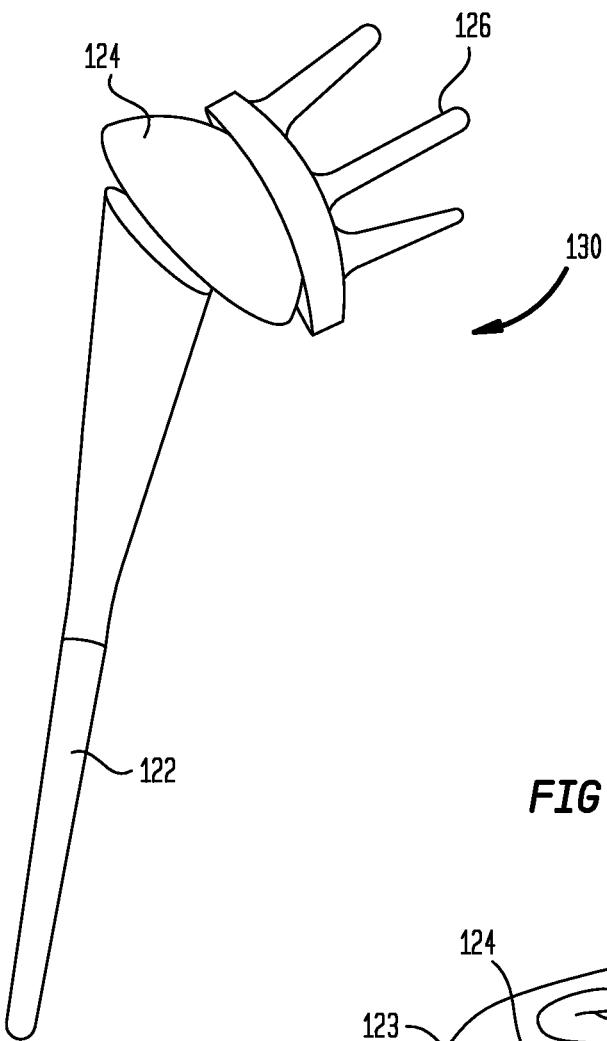
FIGS. 8(a) and 8(b) show shoulder orthopedic implant system 130 and system 130 implanted in a patient, respectively.
Figure 8B:
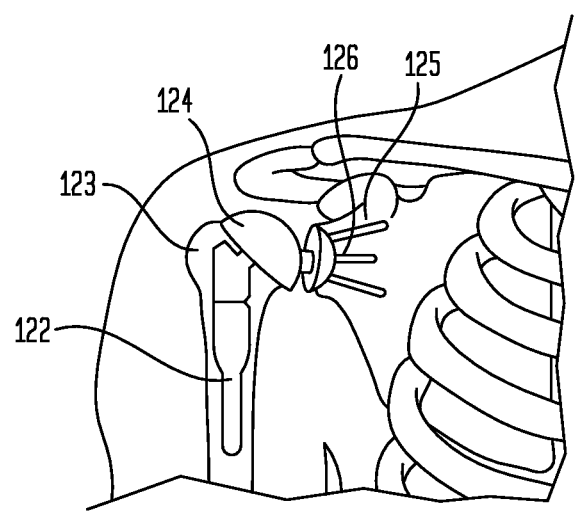

Similarly, shoulder orthopedic implant system 130 shown in FIGS. 8(a) and 8(b) comprising shoulder orthopedic implant stem 122, shoulder orthopedic implant ball and socket 124, and shoulder orthopedic anchor 126 may be implanted, extracted or reoriented or adjusted using surgical instrument 10 described and disclosed herein, with or without impactor 80.

Figure 9:
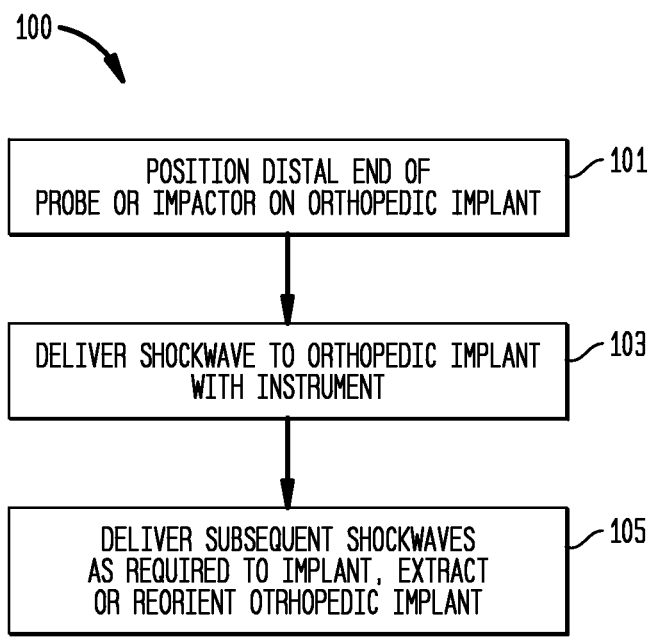
FIG. 9 shows one embodiment of a method 100 for implanting, extracting or reorienting or adjusting an orthopedic implant with instrument 10.

FIG. 9 shows one embodiment of a method 100 for implanting, extracting or reorienting or adjusting an orthopedic implant with instrument 10. At step 101, the distal end of probe 16 or impactor 80 is positioned on a portion of an orthopedic implant that is to be extracted, implanted, or reoriented in a patient. At step 103, a shockwave is delivered by instrument 10 to the orthopedic implant by a user actuating the instrument to deliver the shockwave. At step 105, subsequent shockwaves are delivered to the orthopedic implant by instrument 10 as required to effect the desired extraction, implantation or reorientation. According to various embodiments, method 100 may further comprise any one or more of positioning distal end 17 of probe 16 or the distal end of impactor 80 in contact with at least a portion of the surface of an orthopedic implant, and actuating trigger mechanism 30 to deliver the shockwave to probe 16 and thence to the orthopedic implant, disposing orthopedic implant impactor 80 on distal end 17 of probe 16 and delivering a shock wave to probe 16, impactor 80 thence to the orthopedic implant, and delivering a shock wave to the probe by instrument 10 having a rise time ranging between about 2 microseconds and about 20 microseconds, between about 4 microseconds and about 16 microseconds, between about 6 microseconds and about 10 microseconds, and causing the shock wave delivered by probe 16 or impactor 80 to the orthopedic implant to travel from a first side of the implant to a second opposing side of the implant is less than about 30 microseconds, or less than about 20 microseconds. As noted above, the surface of the orthopedic implant may comprise at least one recess or protrusion disposed thereon that is configured to mateably engage distal end 17 of probe 16 or a portion of impactor 80.

In still further embodiments, an orthopedic implant is configured for use with pneumatic surgical instrument 10 such that the surface of the orthopedic implant comprises at least one recess or protrusion disposed thereon and configured to mateably engage distal end 17 of probe 16 or a portion of impactor 80. Such an orthopedic implant may be, by way of example, one of orthopedic hip implant socket or cup 82, orthopedic hip implant insert 84, orthopedic hip implant liner 86, orthopedic hip implant stem 88, orthopedic hip implant ball 90, orthopedic shoulder implant stem 122, orthopedic shoulder implant ball and socket assembly 124, or orthopedic shoulder implant anchor 126.

In yet further embodiments, an orthopedic implant system is provided comprising an orthopedic implant, pneumatic surgical instrument 10 disclosed and described herein, removable probe 16, orthopedic and orthopedic implant impactor 80.

Orthopedic implants of the type described herein are manufactured and sold by Stryker™, DePuy Medical™, Biomed™, Zimmer™, Smith & Nephew™, Wright Medical™, and numerous other manufacturers. Other orthopedic implants suitable for use with surgical instrument 10 described and disclosed herein include, but are not limited to, spinal cages, knee implants, and other orthopedic implants not specifically enumerated herein. Surgical instrument 10 may also be employed to remove bone plates for massive bone reconstruction.

The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

We claim:

1. A pneumatic surgical instrument, comprising:
   a striker;
   a removable probe mountable on a distal end of the instrument;
   a pressure regulator;
   a self-contained gas cartridge operably connected to the pressure regulator;
   a trigger mechanism comprising a trigger, the trigger mechanism being operably connected to the pressure regulator and to the striker, and
   a monolithic universal orthopedic implant impactor configured to receive the distal end of the probe therein or thereon, the universal orthopedic implant impactor comprising first distal convex surfaces having first compound radii configured to internally engage corresponding concave surfaces of a plurality of different predetermined orthopedic implants having varying shapes and/or radii with respect to one another;
   wherein the instrument is configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and the universal orthopedic implant impactor, the shockwave delivered by the probe having a rise time ranging between about 2 microseconds and about 20 microseconds, the shockwave being substantially repeatable by the instrument when the trigger is actuated again by the user, the instrument being configured to implant, extract or reorient any one of the plurality of different orthopedic implants; and
   wherein the universal implant impactor further comprises second distal concave surfaces interposed between the first convex surfaces having second compound radii configured to externally engage corresponding convex surfaces of the plurality of different predetermined orthopedic implants.

2. The pneumatic surgical instrument of claim 1, wherein the second distal concave surfaces and second compound radii are configured to engage corresponding convex surfaces of any one of the plurality of different predetermined orthopedic implants along a substantially continuous line of contact.

3. The pneumatic surgical instrument of claim 1, wherein the plurality of different orthopedic implants are selected from the group consisting of an orthopedic hip implant socket, an orthopedic hip implant CUP, an orthopedic hip implant liner, and an orthopedic hip implant ball.

4. The pneumatic surgical instrument of claim 1, wherein the instrument is further configured to cause the shock wave delivered by the probe and the orthopedic implant impactor to the orthopedic implant to travel from a first side of the orthopedic implant to a second opposing side of the orthopedic implant is less than about 30 microseconds.

5. The pneumatic surgical instrument of claim 1, wherein the instrument further comprises a removable probe cap configured to receive the proximal end of the probe therein or therethrough, the probe cap being mountable on the distal end of the instrument.

6. The pneumatic surgical instrument of claim 1, further comprising a firing pin disposed between a distal end of the striker and the proximal end of the probe, the distal end of the striker being configured to engage and strike a proximal end of the firing pin.

7. The pneumatic surgical instrument of claim 1, wherein the probe further comprises a shaft having a probe terminus disposed at the proximal end thereof.

8. The pneumatic surgical instrument of claim 7, further comprising a removable probe cap configured to receive the shaft therethrough and to house proximally therefrom within the instrument at least one probe O-ring disposed against a distal surface of the proximal probe terminus, the removable probe cap being mountable on the distal end of the instrument.

9. The pneumatic surgical instrument of claim 8, wherein the probe O-ring comprises nitrile and has a thickness ranging between about 1 mm and about 6 mm.

10. The pneumatic surgical instrument of claim 8, wherein the probe O-ring comprises nitrile and has a thickness ranging between about 2 mm and about 4 mm.

11. The pneumatic surgical instrument of claim 7, further comprising a removable probe cap configured to receive the shaft therethrough and to house proximally therefrom within the instrument a plurality of probe O-rings located near a distal surface of the proximal probe terminus, the removable probe cap being mountable on the distal end of the instrument.

12. The pneumatic surgical instrument of claim 1, wherein the trigger mechanism further comprises a trigger chamber configured to contain the predetermined volume of gas.

13. The pneumatic surgical instrument of claim 1, wherein the trigger mechanism further comprises a trigger handle and a trigger actuator operably couplable to the trigger handle.

14. The pneumatic surgical instrument of claim 1, wherein the pressure regulator further comprises a pin configured to puncture the gas cartridge when the gas cartridge is mounted in or on the instrument.

15. The pneumatic surgical instrument of claim 1, wherein the gas cartridge is a $CO_2$ cartridge.

16. The pneumatic surgical instrument of claim 1, wherein the pressure regulator is further configured to provide pressurized gas to the trigger mechanism at pressures ranging between about 15 bars and about 60 bars.

17. The pneumatic surgical instrument of claim 1, wherein the pressure regulator is further configured to provide pressurized gas to the trigger mechanism at pressures ranging between about 25 bars and about 35 bars.

18. The pneumatic surgical instrument of claim 1, wherein the probe further comprises stainless steel.

19. The pneumatic surgical instrument of claim 1, wherein the probe has a length ranging between about 10 cm and about 30 cm.

20. The pneumatic surgical instrument of claim 1, wherein the orthopedic implant impactor comprises a proximal aperture or recess configured to accept at least a portion of the distal end of the probe thereon or therein.

21. The pneumatic surgical instrument of claim 1, wherein the first distal convex surfaces and first compound radii are configured to engage corresponding concave surfaces of any one of the plurality of different predetermined orthopedic implants alone a substantially continuous line of contact.

* * * * *